United States Patent [19]
Morris, Jr. et al.

[11] Patent Number: 5,932,252
[45] Date of Patent: Aug. 3, 1999

[54] METHOD AND COMPOSITION FOR TREATMENT OF OSTEOPOROSIS

[75] Inventors: R. Curtis Morris, Jr.; Anthony Sebastian, both of San Francisco, Calif.

[73] Assignee: The Regents of the University of California, Oakland, Calif.

[21] Appl. No.: 08/380,449

[22] Filed: Jan. 23, 1995

Related U.S. Application Data

[63] Continuation of application No. 08/188,664, Jan. 28, 1994, abandoned, which is a continuation of application No. 08/042,296, Apr. 2, 1993, abandoned, which is a continuation-in-part of application No. 07/420,597, Oct. 17, 1989, Pat. No. 5,171,583, which is a continuation-in-part of application No. 07/260,856, Oct. 21, 1988, abandoned.

[51] Int. Cl.$^6$ .......................... A01N 59/00; A61K 33/10
[52] U.S. Cl. ............................ 424/717; 424/722
[58] Field of Search ...................... 424/717, 722

[56] References Cited

U.S. PATENT DOCUMENTS

| | | | |
|---|---|---|---|
| 3,541,208 | 11/1970 | Dann, Sr. et al. | 424/601 |
| 3,639,585 | 2/1972 | Hesse | 424/601 |
| 3,708,574 | 1/1973 | Corker | 424/44 |
| 4,259,315 | 3/1981 | Lippmann et al. | 424/153 |
| 4,289,750 | 9/1981 | Kopp et al. | 424/451 |
| 4,405,596 | 9/1983 | Helbig et al. | 424/154 |
| 4,829,549 | 5/1989 | Vogel et al. | 378/55 |
| 4,837,015 | 6/1989 | Olsen | 424/78.1 |
| 4,855,289 | 8/1989 | Wester et al. | 514/171 |
| 4,965,282 | 10/1990 | Takamura et al. | 514/406 |
| 4,966,776 | 10/1990 | Pak | 424/677 |
| 5,171,583 | 12/1992 | Morris, Jr. et al. | 424/717 |
| 5,219,889 | 6/1993 | Walsdorf et al. | 514/574 |
| 5,228,445 | 7/1993 | Pak et al. | 128/660.01 |

FOREIGN PATENT DOCUMENTS

| | | |
|---|---|---|
| 2432869 | 3/1980 | France . |
| 3241765 | 5/1984 | Germany . |

OTHER PUBLICATIONS

Goulding et al J. Urology vol. 133 May 1985 pp. 891–893 Lemann, Jr. Abstract.
Wachman et al., "Diet and Osteoporosis", *Lancet* 2:958–959 (May, 1968).
Barzel et al., "The Effects of Chronic Acid and Alkali Administration on Bone Turnover in Adult Rats", *Clin. Sci.* 36:517–524 (1969).
Barzel, "The Role of Bone in Acid Base Metabolism", *In:* Barzel, U.S., ed. *Osteoporosis*: 199–206, (1970).
Barzel, "Osteoporosis: The State of the Art", *Am. J. Clin. Nutr.* 23 (6):833–840 (Jun., 1970).
Stacy et al., "Acidosis and Hypercalciuria: Renal Mechanisms Affecting Calcium, Magnesium and Sodium Excretion in the Sheep", *J. Physiol.* 210:549–564 (1970).
Barzel, "The Challenge of Osteoporosis", *Arch Phys. Med. Rehabil.* 52(3): 135–137 (Mar., 1971).
Barzel, "Alkali Therapy in Immobilization Osteoporosis", *Israel Journal of Medical Sciences* 7:499 (1972).
Richards et al., "Treatment of Osteomalacia of Renal Tubular Acidosis by Sodium Bicarbonate Alone", *Lancet* 2:994 (1972).
Barzel, "Acid–Induced Osteoporosis: An Experimental Model of Human Osteoporosis", *Calcif. Tissue Res.* 21 Suppl: 417–422 (1976).
Orsatti, 86 *Chem. Abstr.* 41549e (1976).
Orsatti et al., "Effect of Bicarbonate Feeding on Immobilization Osteoporosis in the Rat", *Calcif. Tissue Res.* 21:195–205 (1976).
Kocian et al., "Simultaneous Correction of Ca Deficiency and Acidosis in Fasting Obese Patients as a Prevention of Bone Demineralisation", *Nutr. Metab.* 23:391–398 (1979).
Dietz, et al., "Partial Replacement of Sodium by Potassium in the Diet Restores Impaired Noradrenaline Inactivation and Lowers Blood Pressure in Stroke–prone Spontaneously Hypertensive Rats", *Clin. Sci.* 61:69S–71S (1981).
Ballina et al., "Calcium Metabolism of Intact and Thyroparathyroidectomized Rats Fed a Bicarbonate Enriched Diet", *J. Endocrinol Invest.* 8:171–174 (1985).
Burnell, "Effects of Dietary Alteration of Bicarbonate and Magnesium on Rat Bone", *Am. J. Physiol.* 250:F302–F307 (1986).
Barzel, "Osteoporosis: The State of the Art in 1987: A Review", *Semin. Nucl. Med.* 17(4): 283–292 (Oct., 1987).
Pacifici et al., *N. Engl. J. Med.* 317:1025 (Oct., 1987).
"Osteoporosis" in *Diet and Health Implications for Reducing Chronic Disease Risk*, Natl. Res. Council, Ch. 23 (1989).

*Primary Examiner*—Peter F. Kulkosky
*Attorney, Agent, or Firm*—Townsend and Townsend and Crew LLP

[57] ABSTRACT

A combination of the following active ingredients for treating osteoporosis: (a) a pharmacologically-acceptable alkalinizing potassium salt which produces hydroxyl ions and is thereby capable of reducing the acidity of tissue fluids or urine and which is selected from the group consisting of potassium bicarbonate and potassium salts of carboxylic acids which are transformed to bicarbonate and thus alkalinize in vivo; and (b) a thiazide diuretic.

7 Claims, No Drawings

METHOD AND COMPOSITION FOR TREATMENT OF OSTEOPOROSIS

This is a continuation of application Ser. No. 08/188,664, filed Jan. 28, 1994, now abandoned, which is a Continuation of application Ser. No. 08/042,296, filed Apr. 2, 1993, now abandoned, which is a continuation-in-part of U.S. application Ser. No. 420,597, filed on Oct. 17, 1989, now U.S. Pat. No. 5,171,583 granted Dec. 15, 1992, which was a continuation-in-part of U.S. application Ser. No. 260,856, filed Oct. 21, 1988, now abandoned.

GOVERNMENT SUPPORT

The U.S. government may have certain rights in the invention pursuant to Grant No. NS-23780 awarded by the National Institutes of Health.

FIELD OF THE INVENTION

This invention concerns novel methods for treating osteoporosis in humans and, more particularly, involves a method and composition for treating osteoporosis with a combination of an alkalinizing potassium salt and a thiazide diuretic which is effective in such treatment, which drug combination reduces the health risks or side effects associated with thiazide treatment.

BACKGROUND OF THE INVENTION

Osteoporosis is a metabolic bone disease characterized pathologically by an absolute decrease in the amount of bone, and clinically by increased susceptibility to fractures. Riggs et al., *N. Engl. J. Med.* (1986), 314:1676; Rusbach et al., in: *Textbook of Endocrinology,* Ed(s) Williams, (1981), p. 922; Riggs, in: *Cecil Textbook of Medicine,* Ed(s) Wyngaarden et al., (1985), p. 1456; Riggs et al., *Am. J. Med.,* (1983), 75:899.

There are several biochemical markers which taken together, can be used to either diagnose a patient as osteoporotic, or to study the efficacy of treatments for osteoporosis. For example, urinary hydroxyproline excretion rate is widely used as a marker for bone resorption. Klein et al., *Metabolism* 2, Vol. 13, No. 3, March 1964, 272–285; Charles et al., *J. Clin. Invest.,* Vol. 76, December 1985 2254–2258; and Deacon et al., *Clin. Chim. Acta.,* 1987, 297–306. Pyridinoline and deoxy-pyridinoline, two types of collagen crosslinks present in bone, which can be detected in urine, are also markers for bone resorption. Robins, et al., *European Journal of Clinical Investigation* (1991), 21:310–315.

Serum concentrations of osteocalcin serve as a biochemical marker of the rate of bone formation. Osteocalcin is an integral protein of the organic matrix of bone synthesized by bone-forming cells (osteoblasts) during the process of bone formation. A small fraction of the newly synthesized osteocalcin escapes into the circulatory system, thus providing a blood marker of the rate of bone formation. The osteocalcin concentration increases when the bone formation rate increases, and decreases when the bone formation rate decreases. Brown, et al., *The Lancet,* May 19, 1984, p. 1091, "Serum Bone GLA-Protein: A Specific Marker For Bone Formation In Postmenopausal Osteoporosis". Another reflection of bone resorption/bone formation are changes in calcium and phosphorus balances (positive or negative) which are determined by measuring the difference between the total excretion (feces and urine) and the dietary intake of calcium or phosphorus ion. (These balances are positive when the total excretion is less than the dietary intake.)

Thiazide diuretics are widely used for the treatment of hypertension. In recent years a number of studies have suggested that they may also have a potential role in the prevention of bone loss and osteoporotic fracture, leading to several recent proposals for randomized, controlled clinical trials thereof (Lacroix, *Comprehensive Therapy* (1991), 17(8): 30–39; Editorial, "Thiazide Diuretics and Osteoporosis", BJCP, Autumn 1991, 45(3); Ray, W. A., Editorial, "Thiazide Diuretics and Osteoporosis: Time for a Clinical Trial?", Jul. 1, 1991, *Annals of Internal Medicine* 115(1): 64–65).

The proposals that the thiazide diuretics may be effective in the treatment of osteoporosis are based on the recognition that they reduce urinary calcium excretion (Adland-Davenport et al., *Am. J. Obstet. Gynecol.,* (Jul. 15, 1985), 152(6) Part 1: 630–634; Wasnich et al., *Obstetrics and Gynecology,* (April 1986), 67(4): 457–462; Ray et al., *The Lancet,* (Apr. 1, 1989): 687–690; Steiniche et al., *APMIS,* (1989), 97:302–308; and Lacroix et al., *New Eng. J. Med.,* (Feb. 1, 1990): 286–290), improve calcium balance (Wasnich et al., *New Eng. J. Med.,* (Aug. 11, 1983): 344–347; Hunt et al., *Am. J. Clin. Nutr.,* (1989), 50: 517–523; Steiniche et al., 1989; and La Croix et al., 1990) and decrease bone loss (Wasnich et al., *Br. Med. J.,* (1990), 301: 1303–1305), coupled with the recent reported studies associating thiazide use with a decreased risk of hip fracture (Ray et al., 1989; LaCroix et al., 1990; and Felson et al., *JAMA,* (1991), 265: 370–373).

The thiazide diuretics have, however, been associated with a recognized set of side effects, particularly when administered at higher doses. Administration of the thiazides commonly causes hypokalemia (Bloomfield et al., 1986, *J. Clin. Hypertens,* 4:331–338; Solomon et al., *J. Cardiovasc. Pharmacol.* (1991) 17:854–859). They cause postural hypotension, resulting in increased frequency of fainting, dizziness and loss of consciousness in women (La Croix, 1991; Hale et al., *J. Am. Geriatric Soc.* (1984) 32:5–10). In men, impotence commonly occurs (Papadopoulos, *Arch. Intern. Med.,* Vol. 140, p. 1341 (1980); and Report of Medical Research Council Working Party on Mild to Moderate Hypertension, *The Lancet,* Sep. 12, 1981, pp. 539–543). In addition, they may adversely affect electrolytes, carbohydrate metabolism, lipids and kidney function (Fried et al., in *Diuretics Physiology Pharmacology and Clinical Use,* 1986, Chapter 4, pp. 66–82).

It is therefore desirable to take advantage of the hypocalciuric properties of the thiazide diuretics in the treatment of osteoporotic disease, while avoiding the multiple side effects thereof.

U.S. Pat. No. 5,171,583, granted on Dec. 15, 1992, the contents of which are incorporated herein by reference, discloses a method for ameliorating or preventing osteoporosis in humans afflicted with or predisposed to osteoporosis, comprising administering a composition containing a therapeutically or prophylactically-effective amount of a composition of a pharmaceutically-acceptable alkalinizing potassium salt. An effective dose of the alkalinizing potassium salt of 40–400 mmoles/70 kg patient weight/day and preferably 40–250 mmoles/70 kg/day is disclosed therein.

In accordance with the present invention, when the thiazide diuretics are used in combination with the foregoing alkalinizing potassium salts, a method and composition for treating osteoporosis is provided which reduces if not eliminates hypokalemia and the risks and side effects associated with the use of the thiazides.

SUMMARY OF THE INVENTION

The present invention thus involves a novel method for ameliorating or preventing osteoporosis in humans afflicted with or predisposed to osteoporosis, which comprises administering to a patient an effective dosage of a combination drug comprising the following active ingredients:

(a) a pharmacologically-acceptable alkalinizing potassium salt which produces hydroxyl ions and is thereby capable of reducing the acidity (by increasing the alkalinity) of tissue fluids or urine and which is selected from the group consisting of potassium bicarbonate and potassium salts of carboxylic acids which are transformed (combusted) to bicarbonate and thus alkalinize in vivo; and (b) a thiazide diuretic.

Preferably, the alkalinizing potassium salt is administered in an amount of about 60 to 180 milliequivalents/70 kg patient weight/day, and the thiazide diuretic is administered in amounts ranging from about 10% to about 90% of the minimum usual daily oral diuretic dose in humans.

By combining the pharmacologically-acceptable alkalinizing potassium salt and the thiazide diuretic, unexpectedly superior results are obtained in the treatment of osteoporosis as compared with the results obtained by treatment with either such active ingredient alone. Otherwise stated, it is possible in some instances to decrease the amount of the thiazide diuretic ingredient by as much as 90% without materially diminishing the hypocalciuric effect obtained by it when administered as the sole active ingredient. The combination drug of the present invention thus provides the significant benefit of reducing, if not eliminating, the health risks and side effects which may be associated with administration of the thiazide diuretic.

DETAILED DESCRIPTION OF THE INVENTION

The two active ingredients of the combination drug invention, i.e., (a) the pharmacologically acceptable alkalinizing potassium salt and (b) the thiazide diuretic, may be administered as separate dosage forms in conjunction with one another. Alternatively, and preferably, as described more fully below, the alkalinizing potassium salt may be combined with the thiazide in a unitary dosage form which can be administered to subjects without the need for independent administration of these active ingredients.

As used herein, the terms "treatment" or "treating" cover any treatment of osteoporotic disease, and include: (1) preventing osteoporosis from occurring in a subject who does not have osteoporosis or who has not yet been diagnosed as having it; (2) inhibiting or arresting the development of the disease; or (3) regressing or reversing the osteoporotic state.

As further used herein, the combination drug of the invention is utilized in an "effective dosage" when it causes the following effects in the patient:

(a) it reduces the urinary hydroxyproline excretion rate;

(b) it reduces the urinary collagen crosslink excretion rate; and (c) it increases calcium and phosphorus balances, i.e., makes them less negative or more positive.

As also used herein, the term "collagen crosslinks" means pyridinoline and deoxy-pyridinoline crosslinks.

Finally, as used herein the term "calcium balance" means the difference between the total excretion (feces and urine) of calcium and the dietary intake of calcium ion. Similarly, the term "phosphorus balance" means the difference between the total excretion (feces and urine) of phosphorus and the dietary intake of phosphorus ion.

The alkalinizing potassium salts which may be employed in the process of the present invention are those which, when present in the body fluids, produce hydroxyl ions and are thereby capable of reducing the acidity (increasing the alkalinity) of tissue fluids or urine. A number of pharmaceutically-acceptable alkalinizing potassium salts are known, several of which are set forth in Berg et al., *J. Pharmaceut. Sci.* (1977) 66:1, which is incorporated herein by reference. Given the disclosure herein, it will be well within the ability of one skilled in the art to select and screen pharmaceutically-acceptable alkalinizing salts for the ability to treat osteoporosis using well known methods and techniques. Desirably, a salt will be selected which is therapeutically effective in amounts readily achievable in humans while being relatively well tolerated. Different salts may be chosen depending on particular routes of administration and preferred modes of formulation.

The alkalinizing potassium salts which may be thus administered are preferably selected from the group consisting of potassium bicarbonate ($KHCO_3$) and pharmacologically acceptable, non-toxic potassium salts of carboxylic acids such as potassium gluconate ($C_6H_{11}KO_7$) and potassium citrate ($C_6H_5K_3O_7$). The use of potassium bicarbonate is particularly preferred. The preparation, isolation and purification of these salts are well known to those skilled in the art, as they are commonly employed in a therapeutic setting for a variety of uses other than described herein. Specific procedures for the preparation of such salts are described in general terms in Remington's Pharmaceutical Sciences, Mack Publishing Company, Easton, Pa., 16th Ed., 1982, which is incorporated herein by reference.

The thiazide diuretics useful in the method and composition of the present invention comprise any of those conventionally utilized in the treatment of hypertension. Such agents are identified in Goodman and Gilman, The Pharmacological Basis of Therapeutics, Eighth Edition, 1990, pp. 718–721 and 785–788; and in Drug Evaluations Subscription, AMA Div. of Drugs and Toxicology, 1992, Vol. II—Renal-Urologic Drugs, in Table 5. The disclosures of these references are incorporated by this reference. As used herein, the "thiazide diuretics" include the sulfonamide diuretics, e.g., chlorthalidone, whose pharmacological action is indistinguishable from that of the thiazides (See Goodman and Gilman, supra, at page 718). Preferred thiazide diuretics useful herein include chlorothiazide, hydrochlorothiazide, and chlorthalidone.

The thiazide diuretics are believed to be especially effective in the treatment of osteoporotic disease, in combination with the alkalinizing potassium salts, since they are weak carbonic anhydrase inhibitors which impair hydrogen ion secretion and thus decrease osteoclast resorption of bone. Although carbonic anhydrase inhibitors also produce acidosis, it is believed that the alkalinizing potassium salt prevents acidotic conditions and thus acts synergistically with the preferred thiazide diuretics, minimizing the amount of the latter required to produce a hypocalciuric effect. It should, however, be understood that the present invention is not limited by the foregoing hypothesized mechanism of co-action between the active ingredients of the preferred composition.

Administration of the pharmacologically acceptable alkalinizing potassium salt or the thiazide diuretic ingredients of the combination drug of the present invention may be in pharmaceutical compositions described hereinafter and can be via any of the accepted modes of administration for agents which are known to be useful in the treatment of osteoporosis. Each such ingredient may be administered orally, parenterally, or otherwise. Different active alkalinizing potassium salts or thiazide diuretics may be admixed and simultaneously administered, or benefit may be gained in some instances by their separate, sequential administration.

Depending on the intended mode, the alkalinizing potassium salt ingredient may be in the form of solid, semi-solid or liquid dosage forms, such as, for example, tablets, capsules, pills, powders, granules, crystals, liquids, suspensions, or the like, preferably in unit-dosage forms suitable for administration of relatively precise dosages. Similarly, the thiazide diuretic ingredient may be in the form of a solid tablet, capsule or pill, preferably in unit-dosage forms suitable for administration of relatively precise dosages.

Preferably, the alkalinizing salt and the thiazide active ingredients are combined in a solid unitary dosage form in a tablet, capsule or pill, thus obviating the need for separate administration of these ingredients. The solid combined dosage form may include conventional pharmaceutical carriers or excipients, and, in addition, may include other pharmaceutical agents. Thus, the unit dosage form may be compounded with conventional nontoxic solid carriers such as, for example, pharmaceutical grades of mannitol, lactose, starch, magnesium stearate, talcum, cellulose, glucose, sucrose, magnesium carbonate, and the like. Such compositions may contain about 50–90% of the active ingredients of the present invention, preferably about 70–90%.

Alternatively, the alkalinizing potassium salt ingredient may be administered as a separate dosage form, in conjunction with the administration of the thiazide diuretic. The two drugs may thus be administered on the same schedule or on different schedules in accordance with the normal modes of administration thereof. When the alkalinizing potassium salt ingredient is administered as a separate dosage form, it may be in the form of tablets, pills, capsules, powders, granules, crystals, sustained-release formulations, and the like, with any of the previously listed excipients, or may be administered in a liquid pharmaceutically-administrable composition. Such liquid compositions can be prepared, for example, by dissolving the salt, such as potassium bicarbonate, and optional pharmaceutical adjuvants in a carrier, such as, for example, water, aqueous dextrose, glycerol, and the like, to thereby form a solution or suspension. If desired, the separate alkalinizing salt dosage form may also contain minor amounts of nontoxic auxiliary substances such as pH buffering agents and the like, for example, sorbitan monolaurate, triethanolamine, sodium acetate, triethanolamine oleate, etc. Actual methods of preparing such dosage forms are known, or will be apparent, to those skilled in this art; see, for example, the aforesaid Remington's Pharmaceutical Sciences, Mack Publishing Company, Easton, Pa., 16th Ed., 1982. An active potassium salt ingredient of the combination drug, such as potassium bicarbonate, for example, may be provided as a dietary supplement supplied as pills, as granules or powder applied directly to foodstuffs, or dissolved in drinking water, as convenient means of administration.

Preferably, the thiazide ingredient of the combination drug is administered in a daily dosage equivalent to about 3 to 20 mg of hydrochlorothiazide and the alkalinizing potassium salt is administered in a daily dosage of about 60–180, preferably 60 to 120 milliequivalents. At these levels, the following relative effects are observable in comparison to the effects when the same amount of the thiazide diuretic is separately administered:

(a) a reduction in the urinary hydroxyproline excretion rate (measured as described in the Klein, Charles et al. and Deacon et al. publications described above) by more than 10%;

(b) a reduction in the urinary collagen crosslink excretion rate (measured as described in the Robins et al. publication described above) by more than 10%; and (c) an increase in calcium and phosphorus balances (measured as described in conventional manner), for example, by as much as 10%, or more.

As can be seen from the foregoing, the combination drug of the present invention exhibits a synergistic effect in treating osteoporosis, i.e., the combination of the two drugs is substantially more effective than the same amount of the thiazide when independently administered. Most preferably, the thiazide diuretic ingredient of the combination drug may be administered in an amount equivalent to the daily oral administration of 3 to 20 mg of hydrochlorothiazide, appreciably lower than the usual daily oral diuretic dose in humans. The combination of the present invention incorporating these lower dosages of the thiazide is not only effective in treating osteoporosis, but also significantly reduces the health risks and side effects associated with thiazide diuretics at higher doses. It is generally convenient to supply the foregoing daily dosages in multiple (e.g., 3 to 5) tablets incorporating the active ingredients in suitable excipients and coated with a suitable sustained release coating.

The amount of the thiazide diuretic administered in accordance with the present invention will, of course, be dependent on the potency of the particular thiazide used and the mode of administration. The relative and equivalent potencies of various thiazide diuretics are well known to those skilled in the art. (The equivalent daily diuretic doses of hydrochlorothiazide and other thiazide diuretics are disclosed in Fried et al., 1986, supra, at pp. 68–70 and in Drug Evaluations Subscription, supra; those disclosures are incorporated by reference herein.) For example, 500 mg of chlorothiazide are equivalent to 75 mg of hydrochlorothiazide in terms of hypocalciuric potency and ability to treat osteoporosis. Given the disclosure herein, it will be well within the ability of one skilled in the art to select a thiazide diuretic and a dose level equivalent to the dosages of the particular thiazides described herein.

It will also be appreciated by those having skill in the art that in addition to administering the combination drug described herein, it may be desirable to supplement the patient's calcium intake, if necessary, to maintain it at about 1500 mg of calcium per day.

The following examples illustrate some particularly preferred, non-limiting embodiments of the present invention.

EXAMPLE I

A combination drug tablet is prepared containing the following active ingredients: 3 mg of hydrochlorothiazide and 1.5 grams of potassium bicarbonate. Four such tablets are administered daily, to provide a daily dose of 12 mg of the hydrochlorothiazide and 6.0 grams (60 milliequivalents) of the potassium bicarbonate.

EXAMPLE II

A combination drug tablet is prepared containing the same ingredients as Example I, except that the tablet contains only 0.75 mg of hydrochlorothiazide. Again, four such tablets are administered daily for effective treatment of osteoporosis.

From the foregoing, it will be appreciated that the present invention provides a novel method and composition which effectively treats/prevents osteoporosis in human subjects, with lower health risks and incidence of side effects than would be associated with thiazide diuretics.

Although the present invention has been described in some detail by way of illustration and example for purposes of clarity and understanding, it will be obvious that certain changes and modifications may be practiced within the scope of the appended claims.

What is claimed:

1. A method for treating osteoporotic disease in a human being subject thereto, which comprises administering an effective dosage of the combination of the following active ingredients:

(a) a pharmacologically-acceptable alkalinizing potassium salt capable of reducing the acidity of tissue fluids or urine in vivo, said alkalinizing potassium salt being selected from the group consisting of potassium bicarbonate and potassium salts of carboxylic acid which generates, or is metabolized to bicarbonate ion, after ingestion, which salt is capable of reducing acidity in vivo, and (b) a thiazide diuretic, wherein said combination is effective to increase the calcium balance by at least 10% relative to the effect observed with the same amount of the potassium salt or thiazide diuretic separately administered.

2. The method of claim 1, wherein the thiazide diuretic is selected from the group consisting of chlorothiazide, hydrochlorothiazide and chlorthalidone.

3. The method of claim 1, wherein the alkalinizing potassium salt and the thiazide diuretic are administered in a plurality of unit dosage forms equivalent to a daily dosage of from 30 to 120 milliequivalents of the alkalinizing potassium salt and an amount of the thiazide diuretic equivalent to from 3 to 20 mgs. of hydrochlorothiazide.

4. The method of claim 3, wherein the alkalinizing potassium salt and the thiazide diuretic are administered in separate unit dosage forms.

5. The method of claim 3, wherein the alkalinizing potassium salt and the thiazide diuretic are administered in admixture in a unitary dosage form.

6. The method of claim 5, wherein the unitary dosage form further comprises a pharmaceutically-acceptable carrier.

7. The method of claim 3, wherein the alkalinizing potassium salt is potassium bicarbonate.

* * * * *